(12) United States Patent
Nord et al.

(10) Patent No.: US 8,416,918 B2
(45) Date of Patent: Apr. 9, 2013

(54) APPARATUS AND METHOD PERTAINING TO RADIATION-TREATMENT PLANNING OPTIMIZATION

(75) Inventors: Janne Nord, Espoo (FI); Jarkko Peltola, Tuusula (FI)

(73) Assignee: Varian Medical Systems International AG, Zug (CH)

( * ) Notice: Subject to any disclaimer, the term of this patent is extended or adjusted under 35 U.S.C. 154(b) by 265 days.

(21) Appl. No.: 12/860,466

(22) Filed: Aug. 20, 2010

(65) Prior Publication Data
US 2012/0045035 A1 Feb. 23, 2012

(51) Int. Cl.
*A61N 5/10* (2006.01)
(52) U.S. Cl. ............................................................ 378/65
(58) Field of Classification Search ...................... 378/65
See application file for complete search history.

(56) References Cited

U.S. PATENT DOCUMENTS

| 2009/0041188 A1* | 2/2009 | Keall et al. | 378/65 |
| 2011/0091015 A1* | 4/2011 | Yu et al. | 378/65 |
| 2011/0255665 A1* | 10/2011 | Breedveld | 378/65 |

* cited by examiner

*Primary Examiner* — Glen Kao
(74) *Attorney, Agent, or Firm* — Fitch, Even, Tabin & Flannery LLP

(57) ABSTRACT

A radiation-treatment planning apparatus accesses information regarding a treatment target and at least one operational parameter pertaining to a physical characteristic of a given radiation-treatment platform. The apparatus also accesses information regarding a candidate treatment plan using the given platform. The apparatus then optimizes the candidate treatment plan by permitting, temporarily, discontinuities of the at least one operational parameter as between adjacent ones of a plurality of control points to thereby yield an optimized treatment plan. By one approach, this operational parameter can comprise a speed at which a collimator aperture can be changed. In such a case, the aforementioned discontinuities can comprise discontinuities with respect to the speed at which this aperture can be changed. So configured, these teachings will accommodate temporarily permitting speeds that are too fast to be actually performed by the given radiation-treatment platform.

17 Claims, 2 Drawing Sheets

APPARATUS AND METHOD PERTAINING TO RADIATION-TREATMENT PLANNING OPTIMIZATION

TECHNICAL FIELD

This invention relates generally to radiation-treatment planning.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not discriminate between unwanted structures and adjacent tissues, organs, or the like that are desired or even critical to continued survival of the patient. As a result, radiation is ordinarily applied in a carefully administered manner to at least attempt to restrict the radiation to a given target volume.

Collimators are often used to restrict and form the radiation-therapy beam. Many collimators have an aperture that can be adjusted in one or more dimensions. Adjustable apertures permit, to at least some degree, customization of the radiation-therapy beam's cross section to thereby attempt to better match the requirements of a given target volume. Multi-leaf collimators are an example of such a component. Multi-leaf collimators are comprised of a plurality of individual parts (known as "leaves") that are formed of a high atomic-numbered material (such as tungsten) that can move independently in and out of the path of the radiation-therapy beam in order to selectively block (and hence shape) the beam.

Many treatment plans provide for exposing the target volume to radiation from a number of different directions. Arc therapy, for example, comprises one such approach. In such a case it often becomes useful or necessary to adjust the multi-leaf collimator to accommodate various differences that occur or accrue when moving the radiation source with respect to the target volume. A radiation-treatment plan therefore often provides information regarding useful or necessary adjustments to the multi-leaf collimator(s) during such a treatment.

Such plans are often calculated using an iterative process. Beginning with some initial set of settings, a radiation-treatment planning apparatus iteratively adjusts one or more of those settings and assesses the relative worth of the adjusted plan. An iterative approach such as this is often referred to as "optimizing" the plan (where "optimizing" should not be confused with the idea of identifying an objectively "optimum" plan that is superior to all other possible plans).

Optimizing such a plan can prove challenging as the overall computational requirements can be considerable. As one example in these regards, such a candidate treatment plan often comprises a plurality of control points (pertaining, for example, to collimator leaf settings at each of a plurality of source angles in an arc therapy application setting).

The radiation-treatment platform that will serve to administer the radiation in accordance with the optimized plan has corresponding physical limitations. For example, the source will typically move no faster than some given speed during the treatment and the multi-leaf collimator used during that treatment can only change its aperture settings subject to some maximum speed. A treatment plan that fails to account for such physical characteristics can ultimately be unusable if the aperture settings from one position to the next are physically impossible to achieve.

In some application settings, the time required to work through such iterative calculations can result in vexing delays. These delays, in turn, can lead to expensive and undesirable equipment downtime, patient discomfort, and increased costs.

BRIEF DESCRIPTION OF THE DRAWINGS

The above needs are at least partially met through provision of the apparatus and method pertaining to radiation-treatment planning optimization described in the following detailed description, particularly when studied in conjunction with the drawings, wherein.

Figure 1:
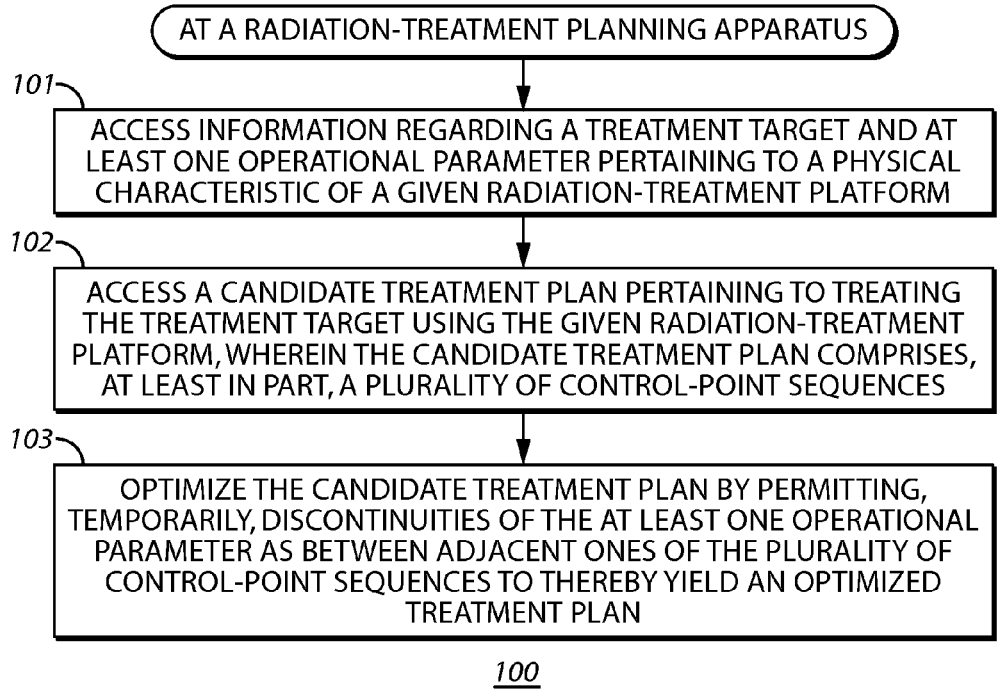
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a radiation-treatment planning apparatus accesses information regarding a treatment target and at least one operational parameter pertaining to a physical characteristic of a given radiation-treatment platform. The planning apparatus also accesses information regarding a candidate treatment plan pertaining to treating the treatment target using the given radiation-treatment platform (wherein the candidate treatment plan comprises, at least in part, a plurality of control points). The planning apparatus then optimizes the candidate treatment plan by permitting, temporarily, discontinuities of the at least one operational parameter as between adjacent ones of the plurality of control points to thereby yield an optimized treatment plan.

By one approach, the aforementioned operational parameter can comprise a speed at which a collimator aperture can be changed. For example, this speed may comprise the speed at which the leaves of a multi-leaf collimator can be changed. In such a case, the aforementioned discontinuities can comprise discontinuities with respect to the speed at which the leaves of the multi-leaf collimator can be changed. So configured, these teachings will accommodate temporarily permitting speeds that are too fast to be actually performed by the given radiation-treatment platform. By one approach, such discontinuities are only permitted when transitioning from one control-point sequence to another and not during any given control-point sequence itself.

Though seemingly counter-intuitive, by permitting an optimization process to at least initially permit discontinuities in these regards can, in fact, result in achieving an acceptable optimized treatment plan in a reduced amount of time. This savings in time can, in turn, lead to reduced equipment downtime, reduced patient discomfort, and reduced costs.

These and other benefits may become clearer upon making a thorough review and study of the following detailed description. Referring now to the drawings, and in particular to FIG. 1, an illustrative process 100 that is compatible with many of these teachings will now be presented.

Figure 2:
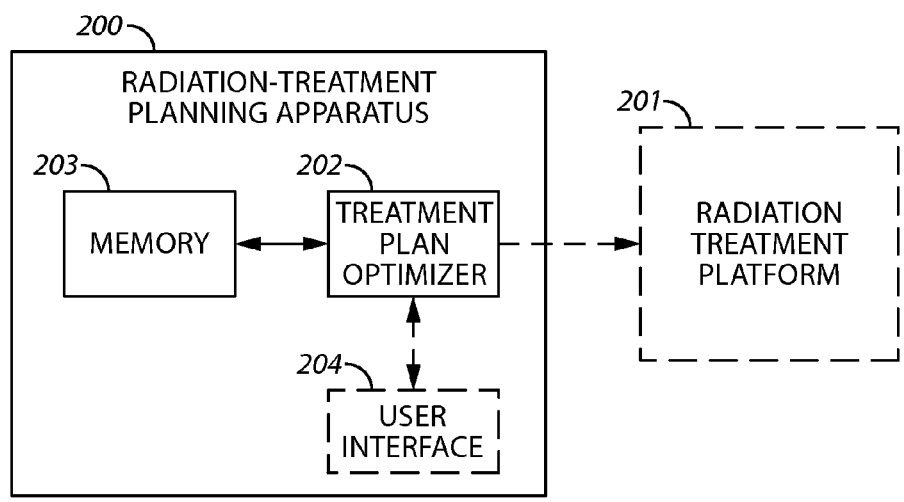
FIG. 2 comprises a block diagram as configured in accordance with various embodiments of the invention.

Those skilled in the art will recognize that these teachings are suitably employed in conjunction with a radiation-treatment planning apparatus. With momentary reference to FIG. 2, such an apparatus 200 works in conjunction with one or more corresponding radiation-treatment platforms 201 (such as, but not limited to, so-called arc therapy platforms as are known in the art). Those skilled in the art will recognize that the radiation-treatment planning apparatus 200 can be physically separated from the radiation-treatment platform 201 as suggested by the illustration. It is also possible, however, for these two components to share a common housing and/or components (in which case the illustration of FIG. 2 can be viewed as a logical rather than a physical rendering).

Such a radiation-treatment planning apparatus 200 comprises a treatment plan optimizer 202 that operably couples to a memory 203. This treatment plan optimizer 203 can comprise a dedicated purpose hard-wired platform or can comprise, in whole or in part, a programmable platform. This treatment plan optimizer 203 is configured (for example, by use of corresponding programming as will be well understood by those skilled in the art) to carry out one or more of the steps, actions, and/or functions described herein.

Those skilled in the art will further understand that the memory 203 can comprise a plurality of memory elements or can be comprised of a single memory element (as is suggested by the illustration). It will also be understood that the memory 203 can comprise a physically discrete component or can comprise a built-in integral part of the treatment plan optimizer 202. Such architectural options are well understood in the art and require no further elaboration here. Generally speaking, this memory 203 serves to store information regarding a treatment target (not shown) (such as a tumor located within a patient) and at least one operational parameter pertaining to a physical characteristic of the radiation-treatment platform 201. So configured, the treatment plan optimizer 202 has access to such information via the memory 203.

If desired, the radiation-treatment planning apparatus 200 can further comprise a user interface 204. This user interface 204 can operably couple to the treatment plan optimizer 202. By one approach, this user interface 204 provides information to an end user. In this case, the user interface 204 can include, for example, signal lights, a display such as a light-emitting diode display, one or more gauges, a hard-copy printer, and so forth. If desired, in combination with the foregoing or in lieu thereof, this user interface 204 can comprise an input mechanism. In this case, and again by way of example and without any intent to suggest any limitations in these regards, the input mechanism can comprise a keyboard, a cursor control device (such as a mouse, a touch pad, a track ball, a joystick, or the like), a touch screen display, a voice-responsive input, and so forth. Various approaches are known in the art in these regards. As these teachings are not overly sensitive to any particular selections in these regards, for the sake of brevity and the preservation of clarity further elaboration in these regards will not be presented here.

Referring again to FIG. 1, this process 100 provides the step 101 of accessing information regarding a treatment target and at least one operational parameter pertaining to a physical characteristic of a given radiation-treatment platform. As noted above, by one approach, this can comprise accessing such information as has been previously stored in a digital computer memory.

For the purposes of this illustrative example, and without intending any particular limitations in these regards, the operational parameter will comprise the speed at which a collimator aperture can be changed. The collimator may comprise, for example, a multi-leaf collimator and hence this speed can comprise the speed (such as the maximum speed) at which the leaves of this multi-leaf collimator can be changed. It will be understood, however, that the operational parameter of interest can of course vary with the application setting and/or the preferences of the system operator. As one example in this regard, the operational parameter of interest can comprise an acceleration constraint as versus a speed constraint. As another example in these regards, the operational parameter can comprise the rate of change for acceleration (sometimes referred to as "jerk") (the latter operational parameter being potentially useful, for example, when the application setting presumes use of a massive movable gantry).

It will also be understood that these teachings can be applied in conjunction with a plurality of different operational parameters of interest. As one simple example in these regards, a first operational parameter can comprise the speed at which a collimator aperture can be changed and a second operational parameter can comprise the corresponding acceleration capability of the collimator's leaves. As another illustrative example in these regards, and again without intending any particular limitations in these regards, in some application settings a first operational parameter of interest can comprise a minimum velocity at which a given movable component of the treatment system is allowed to move. For example, specifying a minimum collimator leaf speed may result in a reduced treatment time. In many application settings it may also be useful to further specify a maximum velocity at which the same component can move (to thereby doubly bound the component by specifying that the component can both move no faster than a first value and further cannot move any less faster than a second value).

Figure 3:
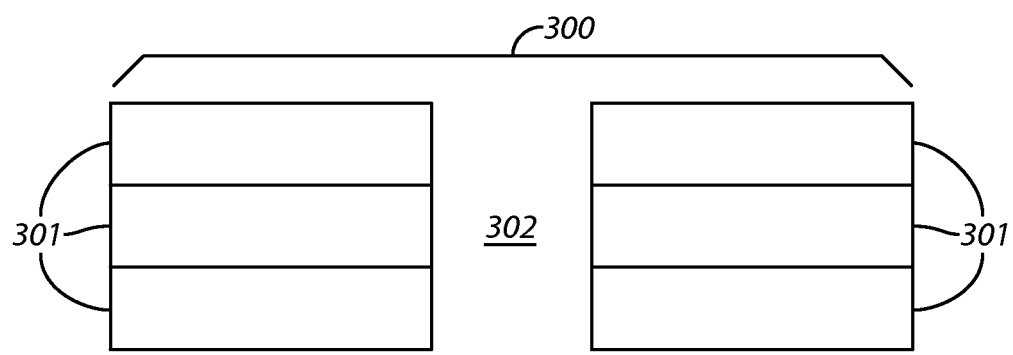
FIG. 3 comprises a front-elevational detail view as configured in accordance with various embodiments of the invention.
Figure 4:
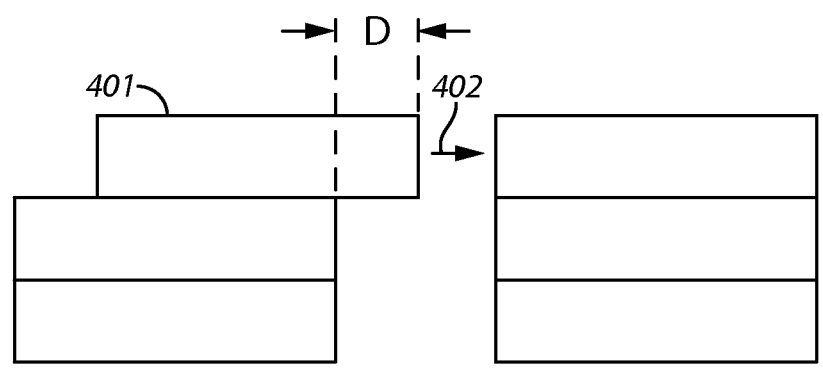
FIG. 4 comprises a front-elevational detail view as configured in accordance with various embodiments of the invention.

To illustrate by way of a simple example, and referring now momentarily to FIGS. 3 and 4, a simplified view of a portion of a multi-leaf collimator 300 reveals a plurality of movable leaves 301 that form, at least in part, a corresponding aperture 302. Over a given amount of time T (such as, for example, 1.0 second), any given one of these leaves (such as the leaf denoted by reference numeral 401) can only move so fast in a given direction (as represented by the arrow denoted by reference numeral 402) and therefore can only move a maximum distance D.

Returning again to FIG. 1, this information can either be obtained from the manufacturer or can be measured in the field as desired. The accessed information can comprise a single value if desired. In such a case, for example, a single speed value would be applied for each leaf and regardless of the leaf's direction of movement. By another approach, a plurality of different values could be accessed to accommodate, for example, leaves that exhibited different speeds from one another and/or leaves that exhibited different speeds depending upon their direction of movement.

This process 100 also provide the step 102 of accessing a candidate treatment plan pertaining to treating the treatment target using the given radiation-treatment platform. Generally speaking, and as is well understood in the art, such a treatment plan comprises, at least in part, a plurality of control points. Modern arc-therapy platforms, for example, often provide for granularity in these regards in the range of from about one degree to about three degrees. Each control point in the treatment plan specifies, for example, settings for the multi-leaf collimator at various treatment angles, radiation emission settings, and so forth.

Pursuant to step 103, this process 100 then optimizes the candidate treatment plan by permitting, temporarily, discontinuities with respect to the at least one operational parameter as between adjacent ones of the plurality of control points to thereby yield an optimized treatment plan. As used herein, this reference to "temporarily" will be understood to reflect that, eventually, this optimization activity must finally take into account the physical limitations of the given radiation-treatment platform and that such discontinuities must therefore be eventually prohibited in order to ensure that the final result is physically attainable.

By one approach, as noted, these discontinuities are temporarily allowed when transitioning from one control point to another. If desired, however, this latitude need not be extended to include the control sequence itself. Accordingly, such discontinuities need not be permitted during the control points themselves.

When the operational parameter comprises the speed at which the leaves of a multi-leaf collimator can be changed, for example, this step 103 can comprise temporarily permitting speeds that are too fast to be actually performed by the given radiation-treatment platform when transitioning from one control point to another. Though possibly counter intuitive, the applicant has determined that such an approach can significantly contribute to rapidly closing in on an acceptable treatment plan result.

By one approach, permitting such discontinuities may be practiced for only a single cycle of the iterative optimization process. By another approach, such discontinuities may be permitted for X cycles where "X" comprises an integer greater than one. These teachings will also accommodate varying the degree to which discontinuities are permitted. For example, by one approach, any discontinuity without limit may be permitted, either initially or so long as any discontinuities are allowed. By another approach, some limit may be imposed to restrict the magnitude of the discontinuity. As one simple example in these regards, discontinuities up to twice the maximum speed at which leaves can be moved may be permitted but nothing greater. These teachings will also accommodate varying such a limit from cycle to cycle. As a simple example in these regards, discontinuities without limit may be permitted during a first optimization cycle, with discontinuities being limited to 4× during the second cycle and 2× during a third and fourth cycle.

As yet another example in these regards, these teachings will also accommodate using a predefined discontinuity distance. To illustrate by way of a non-limiting example, the leaves of a multi-leaf collimator may be allowed to move five centimeters between control points.

These teachings will accommodate other temporary dispensations as pertain to the dynamic adjustment of collimator aperture settings during the optimization process. For example, in combination with the foregoing or in lieu thereof, the optimization step can comprised permitting, temporarily, dynamic adjustments of collimator aperture limits as a function, at least in part, of an angular position as pertains to the radiation-treatment platform. This reference to "angular position" will be understood in context to refer to a particular angular position of the radiation source with respect to the treatment volume during, for example, arc radiation treatment.

By one approach, this dynamic adjustment can comprise increasing the collimator aperture limits at a particular angle. For example, although the actual collimator used with the given radiation-treatment platform may have a maximum aperture opening of, say, five centimeters, the described temporary dispensation may permit that maximum aperture opening to be, say, ten centimeters. By another approach, applied alone or in conjunction with the foregoing, this dynamic adjustment can comprise decreasing the collimator aperture limits at a particular angle.

By one approach, this temporary dispensation can be permitted only during an initial optimization iteration cycle, or only during a few of the initial cycles. In many application settings, however, other approaches in these regards may be beneficial. For example, by one approach, the optimization activity can begin while maintaining the collimator aperture limits and then, during a later mid-term iteration cycle, temporarily permitting the aforementioned dynamic adjustments of the collimator aperture limits. As one specific non-limiting example in these regards, this temporary dispensation can begin after the optimizing activity has begun to converge on a solution while remaining constrained within the collimator aperture limits.

Again, while admittedly potentially counter intuitive, temporarily permitting the optimization activity to accommodate aperture limits that are in fact physically impossible can surprising nevertheless lead to more rapidly converging upon a treatment plan that is useful (and that, of course, makes use of physically-possible aperture limits.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As one example in these regards, these teachings can serve to accommodate temporary variations during the optimization process with respect to a total permitted, planned, and/or possible treatment time. This can comprise, for example, using a radiation-treatment planning apparatus to access information regarding a treatment target and to also access a candidate treatment plan pertaining to treating the treatment target using a given radiation-treatment platform. One can then optimize the candidate treatment plan by permitting, but only temporarily, at least one variation with respect to at least one real-world constraint regarding total treatment time to thereby yield an optimized treatment plan. This can comprise, for example, permitting, temporarily (i.e., only initially and/or subsequent to an initial iterative state but prior to a final iteration), a total treatment time parameter to be longer than is otherwise practical, possible, and/or planned.

We claim:

1. A method comprising:
   by a radiation-treatment planning apparatus:
   accessing information regarding a treatment target and at least one operational parameter pertaining to a physical characteristic of a given radiation-treatment platform;

accessing a candidate treatment plan pertaining to treating the treatment target using the given radiation-treatment platform, wherein the candidate treatment plan comprises, at least in part, a plurality of control points;

optimizing the candidate treatment plan by permitting, temporarily, discontinuities of the at least one operational parameter as between at least some adjacent ones of the plurality of control points to thereby yield an optimized treatment plan.

2. The method of claim 1 wherein the given radiation-treatment platform comprises an arc radiation-treatment platform.

3. The method of claim 1 wherein the at least one operational parameter comprises a speed at which a collimator aperture can be changed.

4. The method of claim 3 wherein the speed at which a collimator aperture can be changed comprises a speed at which leaves of a multi-leaf collimator can be changed.

5. The method of claim 4 wherein the discontinuities comprises discontinuities with respect to the speed at which the leaves of the multi-leaf collimator can be changed, such that, temporarily, the step of optimizing the candidate treatment plan includes permitting speeds that are too fast to be actually performed by the given radiation-treatment platform.

6. The method of claim 1 wherein optimizing the candidate treatment plan further comprises permitting, temporarily, dynamic adjustments of collimator aperture limits as a function, at least in part, of an angular position as pertains to the given radiation-treatment platform.

7. The method of claim 6 wherein permitting, temporarily, dynamic adjustments of the collimator aperture limits comprises beginning the optimizing while maintaining the collimator aperture limits and then temporarily permitting the dynamic adjustments of the collimator aperture limits after the optimizing has begun to converge on a solution within the collimator aperture limits.

8. The method of claim 6 wherein the dynamic adjustments comprise at least one of increasing the collimator aperture limits at a particular angle and decreasing the collimator aperture limits at a particular angle.

9. A radiation-treatment planning apparatus comprising:
a memory having stored therein information regarding a treatment target and at least one operational parameter pertaining to a physical characteristic of a given radiation-treatment platform;
a treatment-plan optimizer being operably coupled to the memory and being configured to:
access a candidate treatment plan pertaining to treating the treatment target using the given radiation-treatment platform, wherein the candidate treatment plan comprises, at least in part, a plurality of control points;
optimize the candidate treatment plan by permitting, temporarily, discontinuities of the at least one operational parameter as between adjacent ones of the plurality of control points to thereby yield an optimized treatment plan.

10. The apparatus of claim 9 wherein the given radiation-treatment platform comprises an arc radiation-treatment platform.

11. The apparatus of claim 9 wherein the at least one operational parameter comprises a speed at which a collimator aperture can be changed.

12. The apparatus of claim 11 wherein the speed at which a collimator aperture can be changed comprises a speed at which leaves of a multi-leaf collimator can be changed.

13. The apparatus of 12 wherein the discontinuities comprises discontinuities with respect to the speed at which the leaves of the multi-leaf collimator can be changed, such that, temporarily, the step of optimizing the candidate treatment plan includes permitting speeds that are too fast to be actually performed by the given radiation-treatment platform.

14. The apparatus of claim 9 wherein the treatment plan optimizer is further configured to optimize the candidate treatment plan by permitting, temporarily, dynamic adjustments of collimator aperture limits as a function, at least in part, of an angular position as pertains to the given radiation-treatment platform.

15. The apparatus of claim 14 wherein the treatment plan optimizer is configured to permit, temporarily, dynamic adjustments of the collimator aperture limits by beginning the optimizing while maintaining the collimator aperture limits and then temporarily permitting the dynamic adjustments of the collimator aperture limits after the optimizing has begun to converge on a solution within the collimator aperture limits.

16. The apparatus of claim 14 wherein the dynamic adjustments comprise at least one of increasing the collimator aperture limits at a particular angle and decreasing the collimator aperture limits at a particular angle.

17. A method comprising:
by a radiation-treatment planning apparatus:
accessing information regarding a treatment target and at least one operational parameter pertaining to a physical characteristic of a given radiation-treatment platform;
accessing a candidate treatment plan pertaining to treating the treatment target using the given radiation-treatment platform, wherein the candidate treatment plan comprises, at least in part, a plurality of control points;
optimizing the candidate treatment plan by:
permitting, temporarily, at least one unconstrained change of the at least one operational parameter as between at least some adjacent ones of the plurality of control points to thereby yield an iterated treatment plan;
further processing the iterated treatment plan while permitting only constrained changes of the at least one operational parameter as between at least some adjacent ones of the plurality of control points to thereby yield an optimized treatment plan.

* * * * *

UNITED STATES PATENT AND TRADEMARK OFFICE
CERTIFICATE OF CORRECTION

PATENT NO. : 8,416,918 B2
APPLICATION NO. : 12/860466
DATED : April 9, 2013
INVENTOR(S) : Janne Nord and Jarkko Peltola It is certified that error appears in the above-identified patent and that said Letters Patent is hereby corrected as shown below:

IN THE CLAIMS:
Claim 13, column 8, line 10, insert --claim-- before "12".

Signed and Sealed this
Thirteenth Day of August, 2013

Teresa Stanek Rea
*Acting Director of the United States Patent and Trademark Office*